United States Patent
Forsell (10) Patent No.: US 11,590,347 B2
(45) Date of Patent: Feb. 28, 2023

(54) SYSTEM FOR TREATING A PATIENT HAVING AN INTESTINAL DISORDER

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 393 days.

(21) Appl. No.: 16/595,091

(22) Filed: Oct. 7, 2019

(65) Prior Publication Data

US 2020/0030603 A1 Jan. 30, 2020

Related U.S. Application Data (63) Continuation of application No. 13/640,795, filed as application No. PCT/EP2011/051898 on Feb. 9, 2011, now Pat. No. 10,434,309.

(30) Foreign Application Priority Data

Apr. 12, 2010 (SE) ...................................... 100364-8

(51) Int. Cl.
| | |
|---|---|
| *A61N 1/36* | (2006.01) |
| *A61F 2/00* | (2006.01) |
| *A61N 1/05* | (2006.01) |
| *A61F 5/445* | (2006.01) |

(52) U.S. Cl.
CPC ........ *A61N 1/36007* (2013.01); *A61F 2/0009* (2013.01); *A61F 2/0036* (2013.01); *A61N 1/0509* (2013.01); *A61F 5/445* (2013.01)

(58) Field of Classification Search
CPC .... A61F 2/0009; A61F 2/0018; A61F 2/0036; A61F 5/445; A61F 2005/4455; A61N 1/0509; A61N 1/36007
See application file for complete search history.

(56) References Cited

U.S. PATENT DOCUMENTS

| | | | | |
|---|---|---|---|---|
| 2004/0122526 A1* | 6/2004 | Imran | ..................... | A61F 5/003 623/23.65 |
| 2004/0122527 A1* | 6/2004 | Imran | ....................... | A61F 2/04 623/23.67 |
| 2007/0255336 A1* | 11/2007 | Herbert | ................. | A61F 5/0026 607/40 |
| 2008/0058887 A1* | 3/2008 | Griffin | ............... | A61N 1/36007 607/40 |

* cited by examiner

*Primary Examiner* — Thaddeus B Cox (57) ABSTRACT

Where an implanted reservoir for intestinal contents is formed from surgically modified intestine that has been cut along a mutual contact line of laterally adjacent sections of a bent portion of intestine and connected so that the resulting upper and lower halves of the intestine form an intestinal wall of the reservoir, the system for emptying such intestinal reservoir comprises an artificial flow control device implantable in the patient's body and adapted to control flow of the intestinal contents from said reservoir, the flow control device comprising at least one pump adapted to act on said intestinal wall so as to reduce the reservoir's volume, thereby emptying the reservoir. The system may further comprise an entry valve upstream of the reservoir and an exit valve downstream from the reservoir. The pump may be an electrical stimulation type pump, a hydraulically acting type pump or/and a mechanically acting type pump.

14 Claims, 6 Drawing Sheets

SYSTEM FOR TREATING A PATIENT HAVING AN INTESTINAL DISORDER

This application is a continuation of U.S. application Ser. No. 13/640,795, filed 21 May 2013, now U.S. Pat. No. 10,434,309, which is the U.S. national phase of International Application No. PCT/EP2011/051898, filed 9 Feb. 2011, which designated the U.S. and claims the priority of Swedish patent application 100364-8, filed 12 Apr. 2010, the entire contents of each of which are hereby incorporated by reference.

BACKGROUND OF THE INVENTION

The present invention relates to a system and method for treating a patient having a disorder related to the patient's intestine. Such disorder may be caused by injury, birth defect, cancer or other diseases, such as constipation or incontinence. More specifically the invention relates to a system and method of regulating the flow through an intestinal reservoir.

In an attempt to overcome such disorders, many different solutions have been proposed. These solutions often include surgery, in particular where a portion of the intestine has to be removed. The reason for such operation may be colorectal cancer, perforated diverticulitis or other kinds of diseases, such as ulceros colitis or Crohns disease. For instance, in the case of ileostoma, jejunostoma, colostoma and rectostoma operations the small intestine (jejunum or ileum) or the large intestine (colon or rectum) is cut and the open end of the healthy portion of the intestine is reattached either to a surgically created stoma in the patient's abdominal wall or, where possible, to the patient's rectum or anus or to tissue adjacent the patient's anus.

The problem then arises to control the intestinal contents flow and, more particularly, to prevent feces from exiting the patient's body uncontrolled. The patient is typically required to excrete into a colostoma bag. This is obviously inconvenient and, in addition, may cause skin irritation since such a bag arrangement requires an adhesive plate to be attached to the patient's skin in order to render the bag liquid tight.

U.S. Pat. No. 4,222,377 suggests the use of an inflatable artificial sphincter comprising a cuff around the anal or urethral canal. A manually operated pump is implanted in the patient's scrotum for inflating and deflating the artificial sphincter.

Similarly, U.S. Pat. No. 5,593,443 discloses an artificial hydraulic anal sphincter under voluntary control. More specifically, the patient may actuate a mechanical or electrical pump for inflating and deflating a cuff. The cuff consists of two parts positioned on opposite sides of the intestine and pressing the intestinal walls together when inflated.

U.S. Pat. No. 6,752,754 B1 discloses an artificial rectum for replacing a portion of a patient's rectum. An inlet of the artificial rectum is operatively connected to the distal end of the patient's large intestine and communicates fecal matter to a macerator-type pump that discharges the feces through an outlet of the artificial rectum connected to the patient's anus. The pump includes a helical screw-type impeller, which when rotated creates shearing effects on the feces, causing it to move down the thread of the screw impeller and discharge through the patient's anus.

An improved system has been described in WO2009/046995 comprising a reservoir in the patient's body for receiving and temporarily collecting therein intestinal contents. In one embodiment the reservoir is surgically created and formed from a plurality of bent portions of the patient's intestine. Laterally adjacent sections of the intestine are cut open along their mutual contact line and the resulting upper halves and lower halves thereof are interconnected so as to form the reservoir. The intestinal reservoir remains within the patient's body when emptying the reservoir. The intestine exits the patients abdominal wall through a surgically created stoma. An exit valve is implanted within the intestine between the intestinal reservoir and the stoma. The exit valve is normally closed by resilient means. An external manually driven suction pump comprising a piston-cylinder-arrangement is used to be temporarily applied from outside the patient's body for emptying the intestinal reservoir, wherein a conduit on the front end of the suction pump is inserted into the intestine, thereby mechanically urging the exit valve to open.

This way of emptying the surgically created intestinal reservoir has been proven unsatisfactory. In particular, although the reservoir remains within the patient's body, an external collecting device has still to be attached, removed and cleaned, similar to the previously described prior art systems.

Other embodiments described in WO2009/046995 overcome this problem by implanting an all artificial reservoir along with a pump acting on the reservoir for emptying the reservoir. Entry and exit valves may be provided in addition to the pump to control the flow of intestinal contents into and from the artificial reservoir. The artificial reservoir with implantable pump substantially improves the patient's living circumstances, because an external collecting device is no longer needed when emptying the reservoir.

Incorporating an artificial reservoir within the patient's natural intestine or at the end thereof is critical. The interconnection between the artificial piece and the intestine's natural tissue will always be subject to the intestine's peristaltic contractions and may therefore fail over time.

SUMMARY OF THE INVENTION

Intestinal Reservoir with Implantable Flow Control Device

According to the invention, a system is provided that acts on an intestinal reservoir, i.e. on a reservoir which is formed from surgically modified intestine that has been cut along a mutual contact line of laterally adjacent sections of a bent portion of intestine and connected so that the resulting upper and lower halves of the intestine form an intestinal wall of the reservoir. The system comprises an artificial flow control device implantable in the patient's body and adapted to control flow of the intestinal contents from said reservoir. The flow control device comprises at least one pump adapted to act on said intestinal wall so as to reduce the reservoir's volume in order to empty the reservoir.

Since the reservoir is made from tissue of the intestine, it is not necessary to connect any artificial piece to living tissue of the patient's natural intestine. Rather is the pump adapted to act on the intestinal wall of the reservoir and can therefore be implanted within the patient's body preferably outside the reservoir. Due to the pump being implanted, an external collecting device need not be attached, removed and cleaned when emptying of the reservoir is desired.

Three preferred basic principles of such pump will be described hereinafter, a mechanical type pump, a hydraulic type pump and an electrical stimulation type pump. These pumps can be combined to cooperate, if desired.

Integrated and Adjacent Location of Pump

According to a first preferred embodiment, components of the pump are adapted for implantation in surgically created folds of said intestinal wall of the reservoir. This is particularly advantageous in relation to the electrical stimulation type pump, as will be described hereinafter.

According to a second preferred embodiment, components of the pump are adapted for implantation inside the patient's body adjacent the reservoir. This is preferable in relation to all three pump types.

In either case, the components of the pump will not come into contact with intestinal contents. However, it is not entirely excluded that a pump is used in context with the present invention that is adapted to be at least partly placed inside the intestinal reservoir.

Electrical Stimulation Type Pump

The electrical stimulation type pump comprises at least one electrical stimulation apparatus adapted to electrically stimulate a muscle or neural tissue of said intestinal wall so as to cause at least partial contraction thereof. This is a very gender way of constricting the reservoir. The electrical stimulation apparatus is preferably adapted to apply electric pulses to the intestinal wall. For this purpose, the electrical stimulation apparatus preferably comprises at least on electrode adapted to generate the electric pulses.

It is particularly advantageous to make use of an electrical stimulation apparatus which is adapted to stimulate different portions of the intestinal wall over time. Thus, different parts of the reservoir can be constricted by stimulation of different intestinal wall portions at different times in any predetermined stimulation pattern. This way, the pump can be adapted to empty the intestinal reservoir by pumping intestinal contents along a section of the reservoir by, over time, electrically stimulating different portions of said intestinal wall in a direction of natural intestinal contents flow.

For this purpose, the electrical stimulation type pump may comprise a plurality of electrodes preferably mounted on one or more holding devices. The holding devices may be in the form of a cable or may have any other shape, however, preferably a longitudinal, stripe-like or rod-like or plate-like shape. A plurality of electrodes may be arranged in one or more rows along the length of the holding devices. The longitudinal holding devices can then be arranged side by side with little or no distance, when implanted, so as to cover substantially the entire intestinal reservoir on one side, preferably on two opposing sides, of the reservoir. This structure and arrangement is particularly suitable for advancing intestinal contents through the reservoir in a controlled manner. For instance, beginning at one end of the reservoir, the "entry", mutually adjacent portions of the intestinal wall and, thus, mutually adjacent sections of the intestinal reservoir can be stimulated consecutively along the length of the reservoir until the respective other end of the reservoir is reached, the "exit", so that the entire reservoir is in a constricted state at the end of the emptying process. Alternatively, the mutually adjacent portions of the intestinal wall can be stimulated in a wave-like manner, i.e. the preceding portion can relax once the next following portion has been stimulated sufficiently. However, the electrodes on the holding devices may likewise be activated all at the same time, thereby simultaneously urging away intestinal contents from all areas of the reservoir. In this case it is particularly important for the system to comprise an entry valve at the upstream end of the intestinal reservoir which has to be closed to prevent back-flow when the electrical stimulation type pump is activated.

The length of the holding devices should be sufficient to substantially span the entire width of the intestinal reservoir, in order to facilitate handling and reduce the number of parts. The perfect length depends on the size of the intestinal reservoir, but is preferably more than 5 cm and can be more than 8 cm or even more than 10 cm.

Handling of a plurality of holding devices can be improved when they are embedded in a flexible web, e.g. integrated within a biocompatible, non-degradable polymer film, such as a polytetrafluoroethylene film. The flexibility of the web allows the holding devices to follow movements of the intestinal reservoir, in particular when sections thereof are constricted individually due to selective electric stimulation.

Instead of embedding the longitudinal holding devices in a flexible web, they may be adapted for implantation in surgically created folds of the intestinal wall of the reservoir. The open side of the folds may be closed by sewing, bonding and/or stapling the tissue of the intestinal wall together so as to form bags for the Longitudinal holding devices carrying the electrodes, preferably after the holding devices have been put in place. The holding devices need not necessarily be longitudinal but may have any other shape, whereby the folds or bags formed from the intestinal wall are suitably formed to accommodate them. The electrodes may of course be directly invaginated in the intestinal wall one by one or in groups without being carried on a common holding device.

Alternatively, instead of providing a plurality of longitudinal holding devices with electrodes, the electrical stimulation apparatus may be formed as an integral unit on at least one side of the reservoir. This makes handling and manufacture even easier. However, an integral unit is relatively stiff, if not entirely rigid, which might be less comfortable for the patient as compared to e.g. the afore mentioned flexible web. Preferably, the integral unit has a size sufficiently large to span an area of 4.5 cm×6 cm, or larger.

Independent of whether the holding devices are thin flexible stripes or just cables leading to the electrodes, or rod-like or plate-like, combined in a flexible web or provided in the form of a stiff or rigid integral unit, they are preferably so adapted that they can be arranged in two planes in order to accommodate the intestinal reservoir between these two planes.

Electrical Stimulation Apparatus Combined with Constriction Device

Alternatively, or preferably in addition to the electrical stimulation type pump, the pump may comprise a constriction type pump implanted in the patient's body for at least partly constricting the intestinal reservoir mechanically or hydraulically by acting from outside on the intestinal wall. Similar to the above described electrical stimulation type pump, the constriction type pump may be adapted to pump intestinal contents along the reservoir by, over time, constricting different sections of the reservoir consecutively or in a wave-like manner in a direction of natural intestinal contents flow. Where individual electrodes of the electrical stimulation type pump, or electrodes carried on one or more holding devices, are combined with constriction devices of the constriction type pump, the electrodes and the constriction devices preferably act on the same portions of the intestinal wall so as to pump the intestinal contents along the reservoir by, over time, electrically stimulating different portions of said intestinal wall and simultaneously constricting respective sections of the reservoir in the direction of natural intestinal contents flow. It is advantageous when the constriction type pump in operation constricts the intestinal reservoir only partly, in order not to damage the intestinal tissue. Complete constriction and, thus, emptying of the reservoir may then be obtained by additionally stimulating the intestinal wall portions electrically in a manner as described before.

It should be noted that, due to the surgical modifications, the intestinal reservoir itself has lost its natural peristaltic capabilities. Therefore, according to a preferred embodiment, the electrical stimulation type pump is adapted to pump intestinal contents along the reservoir in a direction of natural intestinal contents flow by, over time, stimulating different portions of the intestinal wall in a wave-like (peristaltic) manner when constriction of the reservoir caused by the constriction type pump is released. Thereby, the filling of the intestinal reservoir with intestinal contents supplied to the reservoir is improved. This is even useful in cases where the electrical stimulation type pump is not combined with a constriction type pump or with any other pump device. In either case, an exit valve should be provided at the downstream end of the intestinal reservoir, which has to be closed while the reservoir is filling up, to prevent that intestinal contents may escape from the reservoir unintentionally.

From the foregoing it becomes clear that the constriction type pump is adapted to act on said intestinal wall from the outside of the reservoir so as to empty the reservoir by squeezing the reservoir. This can be achieved either hydraulically or mechanically, i.e. by means of a hydraulic type pump or a mechanic type pump.

Hydraulic Type Pump

According to a preferred embodiment, a hydraulic type pump comprises an electrically driven hydraulic pump, a hydraulically acting member for acting on the intestinal wall of the intestinal reservoir from the outside thereof, and an artificial reservoir, wherein the electrically driven hydraulic pump is adapted to pump hydraulic fluid from the artificial reservoir to the hydraulically acting member. The hydraulically acting member may be tube-like or bag-like to accommodate the reservoir therein. This facilitates implantation and ensures proper placement of the hydraulically acting member relative to the intestinal reservoir over long time.

Preferably, the hydraulically acting member comprises a plurality of hydraulic chambers, each chamber acting on a different section of the intestinal reservoir. By filling the chambers in a predetermined sequence, emptying of the reservoir can be controlled.

In a relatively simple structure, each hydraulic chamber is hydraulically interconnected with two other hydraulic chambers, except the first and last chambers which are hydraulically connected to only one other hydraulic chamber and to the artificial reservoir. Thus, fluid can flow from the artificial reservoir sequentially through the hydraulic chambers and back into the artificial reservoir. Preferably, the hydraulic chambers are interconnected by holes acting as throttles for the fluid. This way, fluid will slowly through the chambers, thereby filling the first chambers before the last chambers, so that intestinal contents in the intestinal reservoir are slowly squeezed out of the intestinal reservoir.

However, more sophisticated structures may be used, e.g. involving one or more actively controlled valves between interconnected chambers instead of the passively acting throttles. Also, instead of interconnecting each hydraulic chamber with respective other two of the hydraulic chambers, one or all of the hydraulic chambers may be arranged either such that they are hydraulically isolated from the respective other chambers and connected only to the hydraulic pump via individual hydraulic control lines, or such that they can be hydraulically isolated from the respective other chambers by individually controlling respective valves within the hydraulic path.

The electrically driven hydraulic pump is preferably adapted to evacuate the hydraulically acting member by applying negative pressure, once the intestinal reservoir has been emptied. New filling of the reservoir with intestinal contents is thereby facilitated.

Alternatively, instead of using negative pressure, one can also rely on passive evacuation of the hydraulically acting member. That is, as the intestinal reservoir fills with intestinal contents again, the fluid within the hydraulically acting member surrounding the intestinal reservoir is automatically urged back into the reservoir. This process can be advantageously supported by means of one or more valves between the hydraulically acting member and the artificial reservoir, which, when in an appropriate operational position, allows fluid to passively flow from the hydraulically acting member back into the artificial reservoir when the reservoir fills with intestinal contents and which, when in an appropriate other position, prevents the fluid to flow from the hydraulically acting member back into the artificial reservoir when the intestinal reservoir is being emptied.

Mechanical Type Pump

According to another preferred embodiment, a mechanical type pump comprises at least one mechanically acting member for acting on the intestinal wall from the outside of the intestinal reservoir and an electrical motor adapted to drive the mechanically acting member for emptying the intestinal reservoir.

A preferred structure for the mechanically acting member comprises at least one roller adapted to be rolled over the intestinal reservoir for emptying the reservoir from the outside thereof. For instance, two rollers may act simultaneously on opposite outer surface sides of the intestinal reservoir so as to squeeze the reservoir. Alternatively, one roller may act on one outer surface side of the intestinal reservoir against a counteracting plate arranged on an opposite side of the reservoir. For each roller, two tracks may be provided, one on each Lateral side of the intestinal reservoir, for guiding the roller or rollers when driven by the electrical motor. Thus, the length of the rollers must be sufficient to bridge the width of the intestinal reservoir. Therefore, similar to the length of the holding devices mentioned before, the rollers should have a length of about 10 cm or more and the tracks should preferably also have a length of about 10 cm or more. Preferably, the tracks each have a bent end portion so arranged that it directs away from the reservoir, when implanted. When the roller or rollers are positioned at the track's bent end portion, the intestinal reservoir is not constricted and, thus, intestinal contents can freely enter the intestinal reservoir.

Valve as Part of the Flow Control Device

As mentioned earlier, in addition to the at least one pump, the flow control device is advantageously provided further with one or more valves for controlling flow to and/or from the reservoir. These valves are preferably implanted inside the patient's body outside a section of the patient's intestine and may comprise at least one element adapted to act on the intestine section from the outside thereof so as to act on and, in particular, prevent intestinal contents flow through the intestine section. This valve arrangement is advantageous inasmuch its installment does not require any surgery on the respective part of the intestine.

For instance, an exit valve should be provided downstream of the intestinal reservoir preventing intestinal contents to flow from the reservoir in its closed position.

Preferably, the exit valve is a normally closed valve so that no energy is needed to keep the valve closed during the system's inactive periods.

In addition, an entry valve may be provided allowing intestinal contents to flow towards the intestinal reservoir in its open position. This can be advantageous particularly during the emptying of the reservoir in order to prevent back flow, i.e. when the entry valve is closed. Therefore, the entry valve is preferably a normally open valve. Accordingly, the exit valve and the entry valve are preferably adapted to cooperate such that when one of the two valves is closed, the respective other valve is open, and vice versa.

Exit Valve

The exit valve may comprise a hydraulic or mechanical constriction device for constricting the intestine section so as to keep the intestine section closed. For instance, a hydraulic constriction device may comprise a compartment with a variable volume adapted to open and close the valve by changing the compartment's volume. The compartment preferably has at least one flexible wall defining an opening for the intestine section to pass through, the opening being adapted to close upon increase of the compartment's volume.

Alternatively, or in addition to the hydraulic or mechanical constriction device, the exit valve may comprise at least one electrical stimulation device adapted to electrically stimulate muscle or neural tissue of the intestine section so as to cause at least partial contraction of the intestine section in order to prevent intestinal contents flow through the intestine section. Similar to the stimulation devices of the electrical stimulation type pump described before, the stimulation device of the exit valve may comprise at least one electrode adapted to apply electric pulses to the intestine section. It is particularly advantageous to make use of an electrical stimulation device which is adapted to stimulate different portions of the intestine section over time. Thus, different portions of the intestine section can be constricted by stimulation at different times in any predetermined stimulation pattern, thereby giving the intestine portions currently not stimulated time to recover and, thus, improving the blood circulation in the respective intestine section.

Furthermore, the electrical stimulation device can specifically be adapted to stimulate, over time, the different portions of the intestine section in a wave like manner in a direction opposite to natural intestinal contents flow. As a result, the valve counteracts the natural intestinal contents flow, thereby improving the valve's closing function.

In particular, where the exit valve comprises a constriction device and an electrical stimulation device in combination, the stimulation device and the constriction device can act on the same intestine section in order to keep the intestine section closed. In this case, the constriction device is preferably adapted to only partly constrict the intestine section in the valve's normal (closed) condition, whereas the stimulation device is adapted to stimulate, over time, different portions of the intestine section in a wave like manner in a direction opposite to natural intestinal contents flow so as to urge out-flowing intestinal contents back towards the intestinal reservoir. This is a very gentle way of preventing intestinal contents from exiting the intestinal reservoir.

In addition, the electrical stimulation device is preferably adapted such that it can likewise be used to pump intestinal contents along the intestine section in a direction of natural intestinal contents flow by, over time, stimulating different portions of the intestine section in a wave-like manner. Emptying of the intestinal reservoir can be supported in this manner. During this process, the partial constriction of the intestine section caused by the valve's hydraulic or mechanical constriction device is released.

Entry Valve

The entry valve may be simpler in construction than the exit valve, as the entry valve is preferably a normally open valve. Thus, there is only little danger that the tissue of the intestine section could be damaged due to an unduly long time period of interrupted blood flow. Therefore, the entry valve to be implanted upstream from the reservoir in order to control flow of intestinal contents into the reservoir may substantially consist of a hydraulic or mechanical constriction device for constricting said intestine section at the time when the intestinal reservoir is being emptied.

According to one embodiment of the system, the pump could further comprise a mounting device adapted to be mounted to the peritoneum. The mounting device could be adapted to pass through the peritoneal wall and hold said intestinal section, comprising a flange intended for placement outside the peritoneum. The mounting device could be adapted to hold sutures and staplers passing through the peritoneal wall, when implanted, to hold said artificial intestine section.

Motor

It was already mentioned before, that the pump may comprise a motor for automatically driving the pump. The motor is preferably arranged to be driven by electric or electromagnetic energy. The same or a different motor can be arranged for driving the valve or valves, respectively, between the closed and open positions. A motor in the sense of the present invention is a device that transforms energy other than mechanical energy into mechanical energy.

Preferably, the motor comprises a servo drive. The effect of the servo drive is that a motor with relatively little power and, thus, a relatively small motor can be used, while the time needed to perform the work increases proportionally. However, since the time for emptying the intestinal reservoir is not very critical, this trade off can be accepted.

A manually operable actuator, e.g. a switch, may be provided for activating the pump or the at least one motor, respectively, from outside the patient's body. The switch is preferably arranged for subcutaneous implantation so as to be easily operable from outside the patient's body.

Energy Supply

An energy source may be provided for supplying energy directly or indirectly to at least one energy consuming part of the system, in particular for driving the pump. Preferably, the energy source includes a battery or an accumulator, such as one or more of a rechargeable battery and a capacitor, as an energy storage means. The energy storage means is advantageously adapted for being implanted inside the patient's body.

Energy is preferably transmitted wirelessly. Thus, where the energy source is provided for supplying energy directly or indirectly to at least one energy consuming part of the system, the energy source may comprise a wireless energy transmitter adapted to wirelessly transmit energy from outside the patient's body to the at least one energy consuming part. Alternatively, where the energy source includes a battery or an accumulator, in particular one which is implanted in the patient's body, the energy source may comprise a wireless energy transmitter adapted to wirelessly transmit energy from outside the patient's body to the energy storage means.

Control Unit

It is advantageous to provide a control unit adapted to directly or indirectly control one or more elements of the system, such as for controlling not only the actuation of the pump but also the opening of the exit valve and/or closing of the entry valve, in particular in a manner such that when one of the two valves is closed, the respective other valve is open, and vice versa. The control unit is preferably operable by the patient, e.g. particularly in order to empty the reservoir, such as by actuating the afore-mentioned subcutaneously implantable switch.

Also, the control unit may comprise a first part adapted for implantation in the patient's body and a second part adapted to cooperate with the first part from outside the patient's body. In this case, the control unit can be adapted to transmit data from the external second part of the control unit to the implanted first part of the control unit in the same manner as energy is transmitted to the at least one energy consuming part.

The invention will now be described in more detail in context with some preferred embodiments of the invention as shown in the accompanying drawings.

DETAILED DESCRIPTION OF THE DRAWINGS

Figure 1A:
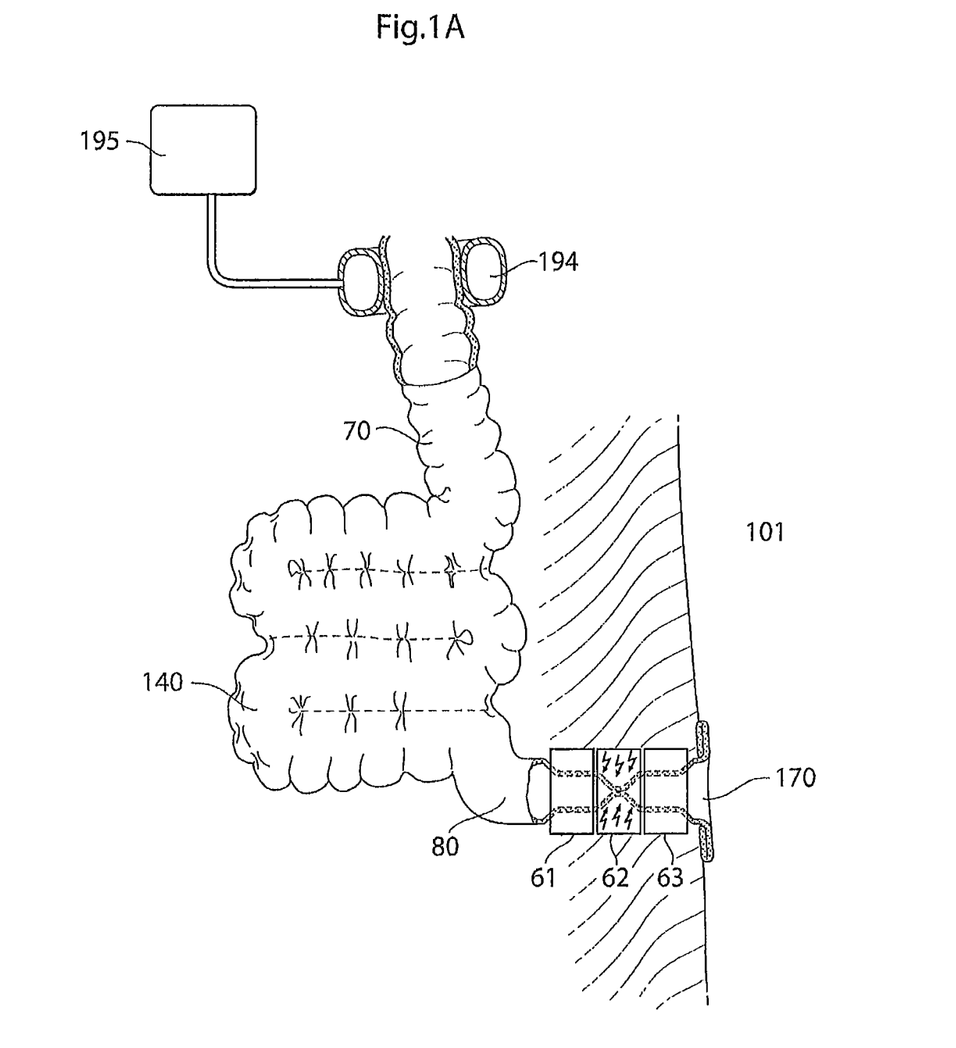
FIG. 1A shows a surgically modified section of a human intestine forming an intestinal reservoir with a deactivated entry valve in front and an activated exit valve behind the intestinal reservoir.

FIG. 1A shows a reservoir 140 formed from human intestine 70. A plurality of bent portions of the human's intestine 70 is cut open along the mutual contact lines of laterally adjacent sections thereof. The resulting upper halves and lower halves are interconnected so as to form the walls of the intestinal reservoir 140. The interconnection can advantageously be made with staplers, possibly including bonding with a biocompatible glue, but sewing is likewise an option.

At the exit of the intestinal reservoir 140, an exit valve comprising a plurality of valve sections 61, 62, 63 is provided along and encloses a non-modified terminate section 80 of the patient's intestine. The non-modified terminate section 80 is passed through the patient's abdominal wall 101 and forms a surgically created stoma 170. The non-modified terminate section 80 could likewise lead to the patient's rectum or anus. The valve sections 61, 62, 63 each comprise an electrical stimulation device adapted to electrically stimulate muscle or neutral tissue of the intestine's terminate section 80 so as to cause at least partial contraction of the terminate section. Electrical stimulation is achieved by applying electrical pulses to the terminate section 80 by means of electrodes (not shown). Each of the valve sections 61, 62, 63 further comprises at least one constriction device.

In FIG. 1A the constriction devices of all three valve sections 61, 62, 63 are activated. As can be seen, the constriction devices 61, 62, 63 only partly constrict the intestine's terminate section 80 so that blood circulation in the tissue of the intestinal wall is not negatively affected thereby. The electrical stimulation devices of the valve sections 61, 62, 63 are adapted to further constrict the terminate section 80 so that flow through the terminate section 80 is completely prevented. However, only one electrical stimulation device is activated at a time. In the situation shown in FIG. 1A, the central valve section 62 is currently activated so as to stimulate and thereby completely constrict the corresponding section of the intestine's terminate section 80. While instead of the three stimulation devices shown, a single stimulation device would be sufficient for opening and closing the intestine, the arrangement of the plurality of stimulation devices allows to stimulate different sections of the intestine's terminate section 80 over time. The function of the three stimulation devices may also be combined in one integral unit. Since the electrical stimulation in each valve section 61, 62, 63 always occurs for a short time period only, the respective other, non-stimulated sections of the intestine's terminate section 80 have time to recover from a previous constriction so that sufficient blood flow within the intestinal wall is ensured. All in all, the valve sections 61, 62, 63 allow for gentle constriction of the intestine's terminate section 80 at the exit of the reservoir when keeping the exit normally closed. Most preferably, closing is achieved by stimulating different sections of the intestine's terminate section 80 in a wave-like manner in a direction opposite to the natural intestine contents flow.

However, instead of combining electrical stimulation devices with a constriction device, the valve at the exit of the reservoir 140 may only be formed by one or a plurality of constriction devices. The constriction device is preferably of the hydraulic type, such as in the form of pressure cuffs, but may also be of the mechanical type. The constriction device is not described here in more detail, and may correspond to the entry valve 194 provided at the entry of the reservoir 140. The entry valve 194 here has the form of a hydraulic cuff. While the valve sections 61, 62, 63 of the exit valve are provided to normally close the exit of the intestinal reservoir 140 in order to keep intestinal contents inside the reservoir 140, the entry valve 194 is normally open to allow intestinal contents to flow into the reservoir 140.

Figure 1B:
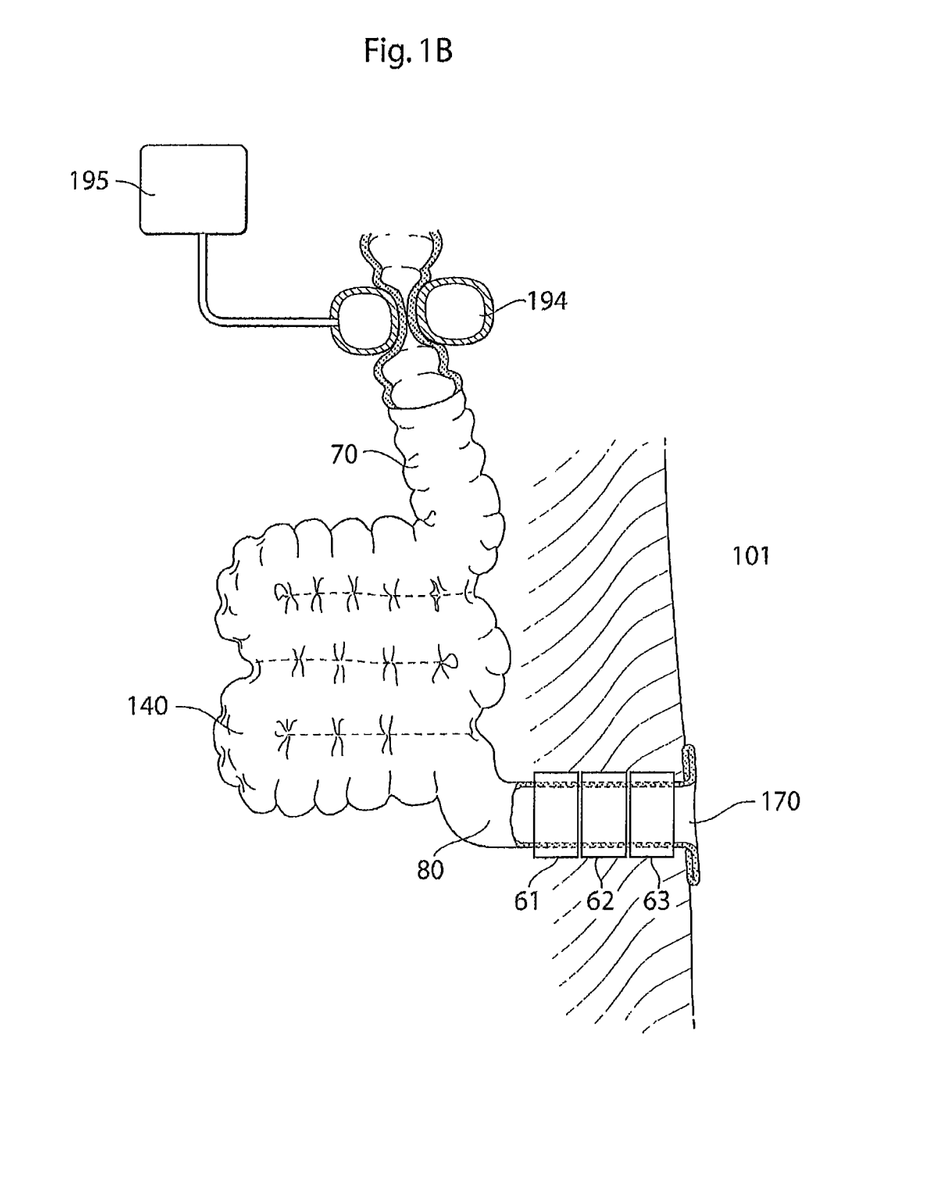
FIG. 1B shows the intestinal reservoir of FIG. 1A with the entry valve activated and the exit valve deactivated.

The cuff of the entry valve 194 can be filled with a hydraulic fluid from an artificial hydraulic reservoir 195 so as to completely constrict the intestine 70 in front of the reservoir 140. This way, backflow of intestinal contents into the intestine 70 may effectively be prevented, when emptying of the reservoir is desired. At the same time, the valve sections 61, 62, 63 of the exit valve are opened to allow emptying of the intestinal reservoir 140. This is shown in FIG. 1B. As can be seen, the partial constriction of the terminal section 80 by means of the constriction devices has been released. Also, electrical stimulation pulses are no longer applied. However, it can be advantageous to support the emptying process by constricting the different sections of the intestine's terminate section 80 in a wave-like manner in a direction towards the stoma 170 by means of the valve sections 61, 62, 63 of the exit valve.

In the following, different embodiments of a system for emptying the intestinal reservoir 140 are described.

Figure 2A:
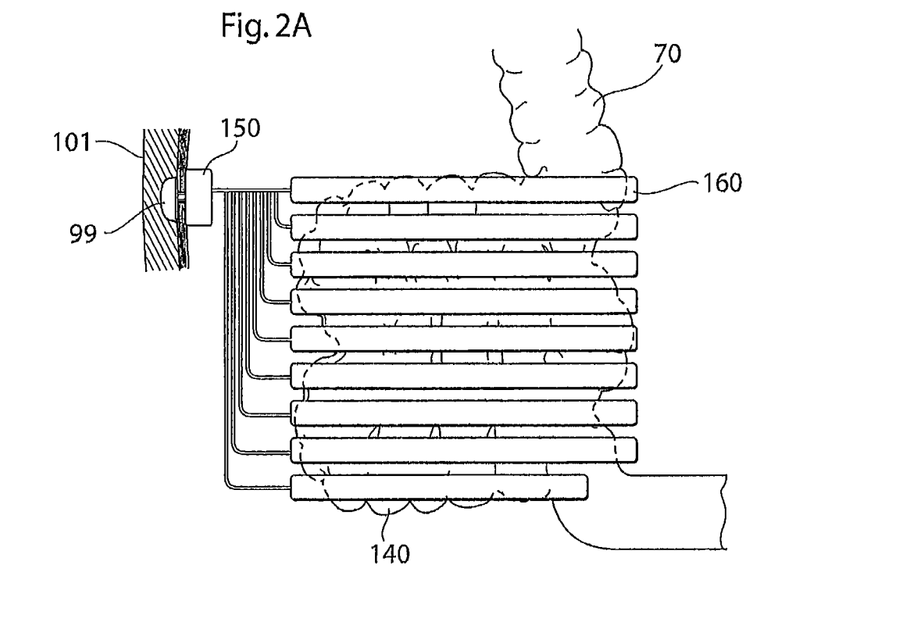
FIG. 2A shows a plan view of an electrical type pump for emptying the intestinal reservoir of FIG. 1B with an electrical stimulation apparatus comprising a plurality of rod-like electrode-carrying holding devices placed side by side adjacent the intestinal reservoir.
Figure 2B:
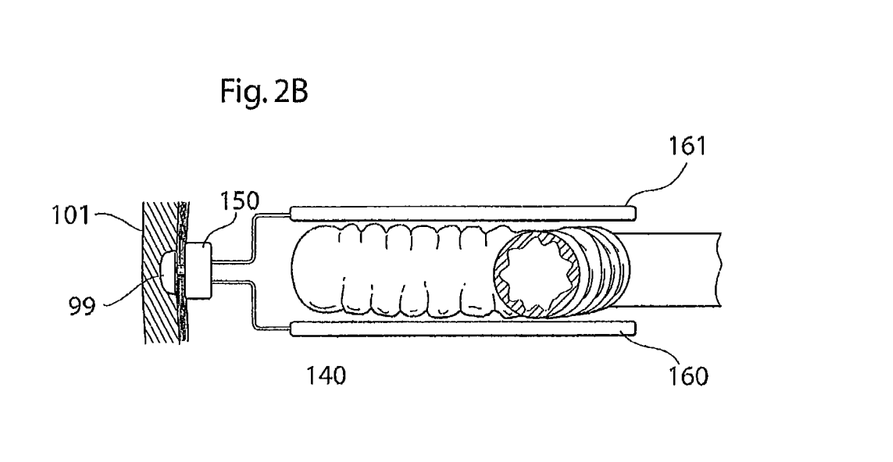
FIG. 2B shows a side view of the electrical type pump of FIG. 2A.

As shown in FIG. 2A, the reservoir 140 may be emptied by means of an electrical stimulation type pump comprising an electrical stimulation apparatus with electrode-carrying holding devices 160 which are adapted to electrically stimulate muscle or neural tissue of the intestinal reservoir 140 so as to cause at least partial contraction of the reservoir 140. This is a very gentle way of constricting the tissue of the intestinal reservoir 140. A second set of electrode-carrying holding devices 161 is arranged on the opposite side of the reservoir 140, as can be seen in FIG. 2B. Thus, the electrodes of the holding devices 160, 161 are arranged substantially in two planes at opposite sides of the reservoir 140. The holding devices 160, 161 have a longitudinal shape so as to span over the reservoir 140 when arranged side by side as shown in FIG. 2A.

As shown in FIG. 2A, the holding devices 160, 161 each have a longitudinal or rod-like shape substantially spanning the entire width of the reservoir 140. The length is preferable 5 cm or longer, depending on the size of the intestinal reservoir, and cane even have a length of more than 8 cm or even more then 10 cm. The overall spanned area would typically be larger than 4.5 cm×6 cm in plan view. The holding devices 160, 161 may each comprise a row of electrodes arranged along the length thereof and adapted to apply electric pulses to the intestinal wall of the reservoir 140. Alternatively, each holding device may substantially consist of only one longitudinal electrode. Preferably, the electrodes can be controlled individually.

In another embodiment, not shown, the stimulation devices 160, 161 may form plate-like members having a larger width than those shown in FIG. 2A, resulting in a decreased number of holding devices. In an even further embodiment, likewise not shown, instead of arranging the holding devices separately side by side, they may be combined in an integral unit, such as a plate, on one side or on opposing sides of the intestinal reservoir. In case that the holding device or devices form plate-like members with an enlarged width, a plurality of electrode rows may be arranged in parallel on the holding devices. The plate-like or rod-like holding devices may be embedded in a flexible web (not shown) to facilitate implantation and relative fixation of adjacent stimulation devices.

Emptying of the intestinal reservoir 140 can be activated by the patient pressing a manually operable actuator 99 subcutaneously implanted in the patient's abdominal wall 101 in the form of a switch. The actuator 99 is connected to a combined energy storage means and controller device 150. The electrodes placed on the holding devices 160, 161 are controlled and supplied with energy via the energy storage means and controller device 150. The device 150 is connected to the holding devices 160, 161 via individual lines.

Under the control of the device 150, different portions of the intestinal wall of the reservoir 140 are stimulated at different times in a predetermined stimulation pattern by means of the electrodes of the holding devices 160, 161 and, thus, different sections of the intestinal reservoir 140 are constricted by such stimulation. The electrical stimulation type pump is specifically adapted to stimulate, over time, respectively adjacent portions of the intestinal wall of the reservoir 140 in a consecutive or wave-like manner in a direction towards the stoma 170 (or rectum/anus) to cause the reservoir 140 to be emptied. This structure allows for adapting the arrangement of the holding devices 160, 161 and their mode of operation to the individual form of the intestinal reservoir 140. This functionality is further enhanced where each of the holding devices 160, 161 carries a plurality of electrodes that are controlled individually or in groups.

As stated before, the entry valve 194 is preferably closed during the emptying of the reservoir. This is particularly important in case that all holding devices 160, 161 are activated simultaneously so as to constrict all sections of the reservoir 140 at the same time. Since the exit valve 194 is closed, intestinal contents cannot flow back from the reservoir into the patient's intestine but are urged towards the exit of the reservoir. An entry valve is not specifically needed when the electrode-carrying holding devices are activated in a consecutive or wave-like manner, as mentioned before, in.

Figure 3A:
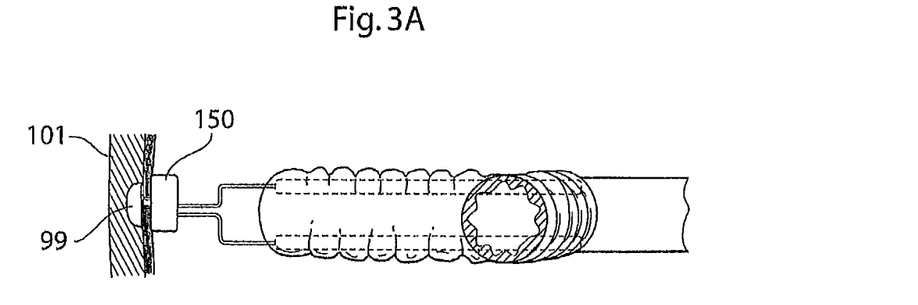
FIG. 3A shows a side view of a variant of the electrical type pump of FIG. 2B with the plurality of the electrode-carrying holding devices placed side by side in folds formed by the wall of the intestinal reservoir.
Figure 3B:
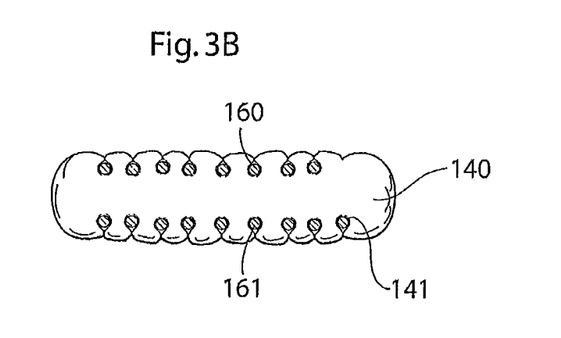
FIG. 3B shows the variant of the electrical type pump of FIG. 3A in a different, cross-sectional side view.

In another embodiment shown in FIGS. 3A and 3B, the electrode-carrying holding devices 160, 161 are specifically provided for being embedded in folds or invaginations 141 surgically created in the intestinal wall of the reservoir 140. By providing the invaginations 141 in the reservoir 140, the holding devices 160, 161 are substantially surrounded by tissue of the reservoir 140 and, thus, contact area is increased. Stimulation of the reservoir 140 can thus be improved. Furthermore, surrounding tissue in the abdominal cavity is not contacted by the electrodes of the holding devices and, thus, not influenced by the stimulation process. Fixation of the holding devices 160, 161 is also improved, thereby ensuring that the holding devices 160, 161 and, thus, the electrodes are precisely located over long time. The holding devices 160, 161 necessarily follow all movements of the intestinal wall of the reservoir 140.

Alternatively, or even in addition to the electrical stimulation type pump, a constriction type pump may be implanted in the patient's body for constricting the reservoir 140 mechanically or hydraulically from outside the intestinal wall of the reservoir 140. Examples of mechanical and hydraulic constriction type pumps will be described in more detail hereinafter in relation to FIGS. 4A, 4B and FIGS. 5A, 5B. Where the stimulation type pump is combined with a constriction type pump, the two pumps preferably act on the same portion of the reservoir 140. In that case, it is advantageous if the constriction type pump constricts the respective portion of the reservoir 140 only partly, in order not to damage the intestine, whereas further constriction is achieved by simultaneous electrical stimulation of the same portion.

In addition, when constriction of the reservoir 140 caused by the constriction type pump is released, the stimulation type pump may, if accordingly adapted, be used to pump intestinal contents towards the exit of the reservoir 140 by, over time, stimulating different portions of the intestinal wall of the reservoir 140 in a wave-like manner in a direction of natural intestinal contents flow. In this way, filling of the reservoir 140 is supported, since intestinal contents do not remain in the area of the entrance of the reservoir 140 but are transported in the direction towards the exit.

Figure 4A:
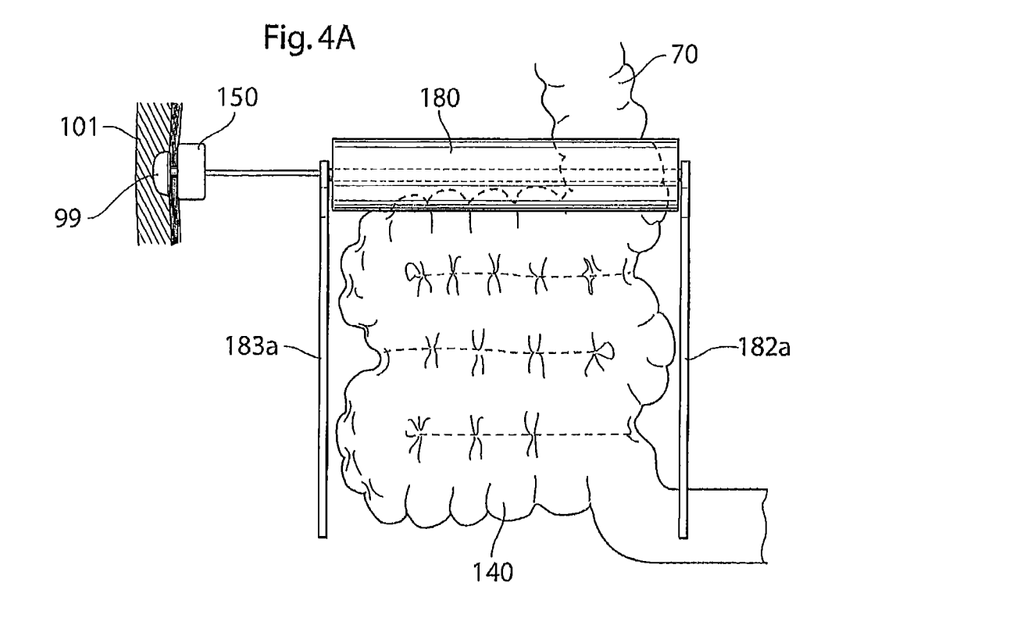
FIG. 4A shows a plan view of a mechanical type pump for emptying the intestinal reservoir of FIG. 1B.
Figure 4B:
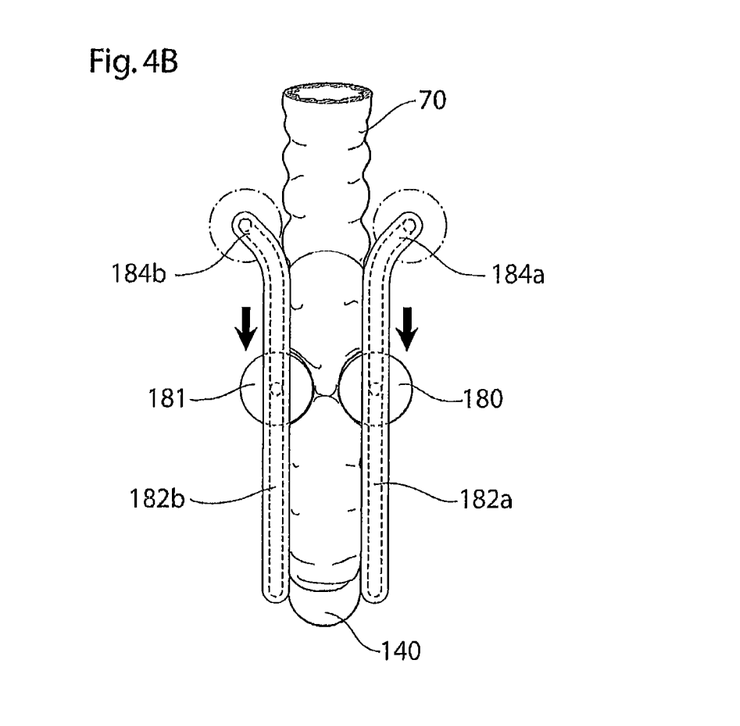
FIG. 4B shows a side view of the mechanical type pump of FIG. 4A.

FIGS. 4A, 4B show an embodiment of a mechanical type pump comprising mechanically acting members in the form of rollers 180, 181 for emptying the reservoir 140. The rollers 180, 181 are arranged on opposite sides of the reservoir 140 and have a length spanning the entire width of the reservoir 140, i.e. 10 cm or more. The rollers are each guided by two tracks 182a, 183a and 182b, 183b, respectively, and are driven by a motor integrated in the rollers (not shown) which preferably comprises a servo drive. The servo drive reduces the force required to move the rollers 180, 181, so that a relatively small motor can be used in exchange for a longer emptying process. The tracks 182a, 183a, 182b, 183b are arranged in pairs on opposite sides of the reservoir 140. As can be seen from FIG. 4B, the tracks have bent end portions 184a, 184b directed away from the reservoir 140 so that the rollers 180, 181 can assume an inactive position in which they do not constrict the reservoir 140. When emptying of the reservoir is desired, the rollers 180, 181 are driven along the tracks in the direction of the arrows, thereby approaching each other and constricting the reservoir 140. When the rollers are further guided by the tracks along the length of the reservoir in their proximate position, they mechanically squeeze intestinal contents in the direction towards and out of the exit of the reservoir 140. When the rollers 180, 181 have reached their final position and the reservoir 140 is emptied, they are returned to their initial inactive position at the end portions 184a, 184b of the tracks. Instead of rollers on each side of the reservoir 140, it can be sufficient to provide one or more rollers only on one side of the reservoir 140 and place a counteracting plate on the respective opposite side of the reservoir 140.

Again, emptying of the intestinal reservoir 140 can be activated by the patient pressing the manually operable actuator 99 subcutaneously implanted in the patient's abdominal wall 101, the actuator 99 being connected to the combined energy storage means and controller device 150. Energy is supplied from the device 150 to the motor or motors inside the rollers 180, 181.

Figure 5A:
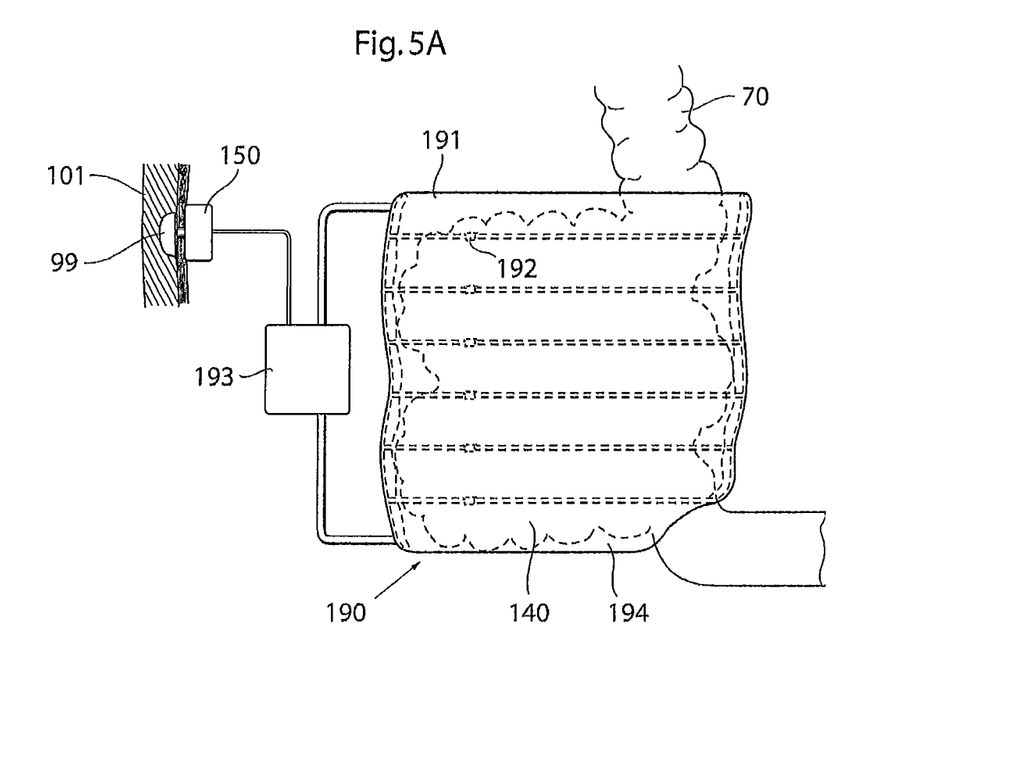
FIG. 5A shows a plan view of a hydraulic type pump for emptying the intestinal reservoir of FIG. 1B.
Figure 5B:
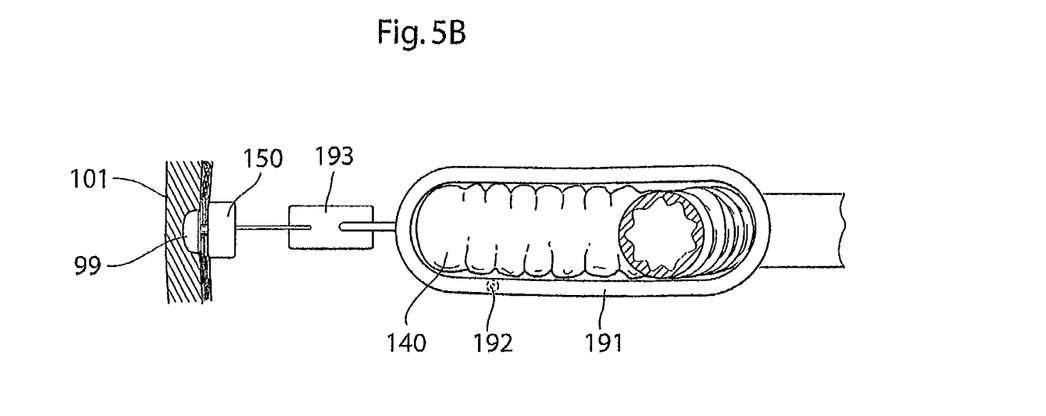
FIG. 5B shows a side view of the hydraulic type pump of FIG. 5A.

FIGS. 5A, 5B show an embodiment of a hydraulic type pump comprising a hydraulically acting member 190 adapted to act on the intestinal wall of the reservoir 140 from the outside thereof. The hydraulically acting member 190 is connected to an artificial reservoir 193 supplying the hydraulically acting member 190 with hydraulic fluid. The artificial reservoir 193 is of a size sufficiently large to accommodate hydraulic fluid in an amount corresponding to the volume of the intestinal reservoir 140. The artificial reservoir 193 has a flexible wall to allow the hydraulic fluid to be drawn off from and to be filled back into the artificial reservoir 193. The hydraulically acting member 190 is of flexible material and may be tube-like or bag-like so as to accommodate therein the intestinal reservoir 140. As shown in FIG. 5B, the reservoir 140 is surrounded by the hydraulically acting member 190. The hydraulically acting member 190 is divided into a plurality of chambers, wherein a first chamber 191 and a last chamber 194 are connected to the artificial reservoir 193 by hydraulic conduits. The chambers are interconnected via connections 192, which may be simple holes acting as a throttle or may include one or more valves that are preferably automatically controlled.

Upon activation of the system by the patient using the subcutaneous actuator 99, emptying of the intestinal reservoir 140 is started by supplying hydraulic fluid from the artificial reservoir 193 to the first chamber 191. The next following chambers are supplied with the hydraulic fluid through the connections 192, thereby causing the hydraulically acting member 190 to be filled slowly from the first chamber 191 to the last chamber 194. The filling of the chambers occurs sequentially, with the next following chamber starting to fill before the foregoing chamber is filled completely. In this manner, intestinal contents are hydraulically squeezed out in the direction towards the exit of the reservoir 140. When the hydraulically acting member 190 is completely filled with hydraulic fluid, the reservoir 140 is completely constricted. The hydraulic fluid is then withdrawn from the chambers of the hydraulically acting member 190 back into the artificial reservoir 193 using negative pressure. The intestinal reservoir 140 may then start to fill up with intestinal contents again.

Again, this process is controlled by the device 150, which is connected to the artificial reservoir 193. Connected to or integrally formed with the artificial reservoir 193 is an electrically driven pump (not shown) for pumping the hydraulic fluid into and withdrawing the hydraulic fluid from the hydraulically acting member. The electrically driven pump is supplied with energy from the combined energy storage means and control device 150.

In another embodiment, each chamber of the hydraulically acting member 190 may have separate fluid connection to the artificial reservoir 193 in order to be able to be filled individually. The intestinal reservoir 140 may be emptied by consecutively filling two adjacent chambers of the hydraulically acting member 190, i.e. first filling the first and second chamber, then emptying the first chamber while filling the third chamber, then emptying the second chamber while filling the fourth chamber, and so forth. In this manner intestinal contents are squeezed towards and out of the exit of the intestinal reservoir 140.

Alternatively, instead of applying a negative pressure for evacuating the chambers, at least one valve, preferably two valves, may be provided (not shown) between the hydraulically acting member 190 and the artificial reservoir 193 which, when in an appropriate operational position, allows the hydraulic fluid to passively flow from the hydraulically acting member back into the artificial reservoir 193 when the intestinal reservoir 140 fills with intestinal contents and which, when in an appropriate other position, prevents the hydraulic fluid to flow from the hydraulically acting member back into the artificial reservoir when the intestinal reservoir is being emptied.

As in all embodiments, emptying of the reservoir 140 is coordinated with the opening and closing of the entry valve 194 and exit valves 61, 62, 63.

Energy Transmission

An energy source may be provided for supplying energy directly or indirectly to at least one energy consuming part of the system, in particular for driving the pump or the motor of the pump. Preferably, the energy source includes a battery or an accumulator, such as one or more of a rechargeable battery and a capacitor, as an energy storage means. The energy storage means is advantageously adapted for being implanted inside the patient's body, as in the case of the afore mentioned combined energy storage means and control device 150.

Energy is preferably transmitted wirelessly. Thus, where the energy source is provided for supplying energy directly or indirectly to at least one energy consuming part of the system, the energy source may comprise a wireless energy transmitter adapted to wirelessly transmit energy from outside the patient's body to the at least one energy consuming part. Alternatively, where the energy source includes a battery or an accumulator, in particular one which is implanted in the patient's body, the energy source may comprise a wireless energy transmitter adapted to wirelessly transmit energy from outside the patient's body to the energy storage means.

Where energy is not transmitted wirelessly, galvanic coupling elements may be provided at least between the accumulator and the energy consuming part, in particular the motor, for transmitting energy to the motor in contacting fashion.

Preferably, in order to reduce the number of parts and possibly increase the system's efficiency, the energy consuming part, in particular the motor, can be adapted to directly transform the wirelessly transmitted energy from the accumulator into kinetic energy. In the alternative, the energy consuming part will have to comprise a transforming device for transforming the wirelessly transmitted energy from the accumulator into electric energy.

Similarly, the system preferably comprises an implantable energy transforming device for transforming the wirelessly transmitted energy from outside the patient's body into energy to be stored in the accumulator of the implanted system and further comprises a wireless energy transmitter adapted to wirelessly transmit energy from outside the patient's body to said implantable energy transforming device.

It is further preferred to set up the system such that the energy consuming part is driven with the electric energy, as said energy transforming device transforms the wireless energy into the electric energy.

The energy transmitter can be adapted to generate an electromagnetic field, a magnetic field or an electrical field. The wireless energy may be transmitted by the energy transmission device by at least one wireless signal. More specifically, the energy transmitter may be adapted to transmit the energy by at Least one wireless energy signal, which may comprise an electromagnetic wave signal, including at least one of an infrared light signal, a visible light signal, an ultra violet light signal, a laser signal, a microwave signal, an X-ray radiation signal, and a gamma radiation signal. Also, the wireless energy signal may comprise a sound or ultrasound wave signal. Furthermore, the wireless energy signal may comprise a digital or analog signal or a combination thereof.

Primary Energy Source

A primary energy source may be provided for charging the energy storage means with energy from outside the patient's body. The primary energy source is preferably adapted to being mounted on the patient's body.

Energy Transmission Feedback

A feedback subsystem, which can make part of a control device described subsequently, can advantageously be provided to wirelessly send feedback information related to the energy to be stored in the energy storage means from inside the human body to the outside thereof. The feedback information is then used for adjusting the amount of wireless energy transmitted by the energy transmitter. Such feedback information may relate to an energy balance which is defined as the balance between an amount of wireless energy received inside the human body and an amount of energy consumed by the at least one energy consuming part. Alternatively, the feedback information may relate to an energy balance which is defined as the balance between a rate of wireless energy received inside the human body and a rate of energy consumed by an energy consuming part.

Control Unit

It is advantageous to provide a control unit adapted to directly or indirectly control one or more elements of the system, such as for controlling opening of the exit valve and/or closing of the entry valve in combination with the pump, in particular in a manner such that when one of the two valves is closed, the respective other valve is open, and vice versa.

At least part of the control unit may be adapted to be implantable in the patient's body. For instance, as described before, a manually operable actuator 99 in the form of a switch may be provided for activating the control unit, the switch preferably being arranged for subcutaneous implantation so as to be operable from outside the patient's body. Alternatively, the control unit may comprise a first part adapted for implantation in the patient's body and a second part adapted to cooperate with the first part from outside the patient's body. In this case, the control unit can be adapted to transmit data from the external second part of the control unit to the implanted first part of the control unit in the same manner as energy is transmitted by said wireless energy transmitter from outside the patient's body to said implantable energy transforming device.

That is, the second part of the control unit may be adapted to wirelessly transmit a control signal to the implantable first part of the control unit for controlling the at least one energy consuming part from outside the patient's body. Also, the implantable first part of the control unit may be programmable via the second part of the control unit. Furthermore, the implantable first part of the control unit may be adapted to transmit a feedback signal to the second part of the control unit.

Sensor

Furthermore, a physical parameter sensor adapted to directly or indirectly sense a physical parameter of the patient can be provided. The physical parameter sensor may be adapted to sense at least one of the following physical parameters of the patient: a pressure within the artificial intestine section, a pressure within the patient's natural intestine, an expansion of the artificial intestine section, a distension of an intestinal wall of the patient's natural intestine, a movement of the patient's intestinal wall.

Similarly, a functional parameter sensor adapted to directly or indirectly sense a functional parameter of the system can be provided, wherein the functional parameter sensor may be adapted to sense at least one of the following functional parameters of the system: a pressure against a part of the system such as the artificial intestine section, a distension of a part of the system such as a wall of the artificial intestine section, an electrical parameter such as voltage, current or energy balance, a position or movement of a movable part of the system.

Preferably, an indicator is coupled to the sensor or sensors, the indicator being adapted to provide a signal when a sensor senses a value for the parameter beyond a predetermined threshold value. The sensor signal may comprise at least one of the following types of signals: a sound signal, a visual signal.

Through-Flow Arrangement of Reservoir

The intestinal reservoir has an upstream part with a first intestinal opening and a downstream part with a second intestinal opening.

The system may include a first intestinal passageway in flow communication with the first intestinal opening arranged for transferring intestinal contents to the reservoir and/or the system may comprise a second intestinal passageway in flow communication with the second intestinal opening, said second intestinal passageway being arranged for transferring intestinal contents from the reservoir. The second intestinal passageway may be surgically connected to a surgically created stoma, in which case the pump is adapted to pump intestinal contents from the reservoir out through said stoma. For instance, the downstream part of the second intestinal passageway may be advanced through the abdominal wall and skin, thereby achieving an intestinal stoma. Alternatively, the second intestinal passageway may be surgically connected to the patient's anus or to tissue adjacent the patient's anus, in which case the pump is adapted to pump the intestinal contents out through the patient's anus.

The reservoir may be made of the small intestine or the reservoir may be made of the large intestine. Accordingly, the second intestinal passageway may be made of the small intestine or the large intestine.

In yet another embodiment, the second intestinal passageway may also be surgically connected to an artificial intestinal piece, wherein said artificial intestinal piece may comprise a valve for controlling the flow of intestinal contents. The artificial intestinal piece may be adapted to be connected to the patient's small intestine or to the patient's large intestine or to the patient's anus or to tissue adjacent the patient's anus or to a surgically created stoma.

Method of Treatment (Implantation)

The invention does not only relate to the system described above, but also to a method of implanting the system or at least components thereof within the patient's body.

As mentioned before, the reservoir of the system is made from the patient's intestine. A respective surgical method of treating the patient therefore comprises the steps of:

cutting the patient's skin and abdominal wall,
dissecting an area of the patient's intestine,
cutting the patient's intestine along a mutual contact line of laterally adjacent sections of a bent portion thereof and connecting by suturing and/or stapling the resulting upper and lower halves of the intestine so as to form an intestinal wall of a reservoir,
implanting at least a pump as part of a flow control device so as to permanently reside inside the patient's body and to act on said intestinal wall so as to reduce the reservoir's volume in order to empty intestinal contents from the reservoir to outside the patient's body, and
thereafter, permanently closing the abdominal wall and skin.

A respective laparoscopic surgical method of treating the patient comprises the steps of:

making a small opening in the patient's skin and abdominal wall,
introducing a needle in the abdominal cavity,
inflating the abdominal cavity with gas,
inserting at least one trocar into the cavity,
introducing a camera through the trocar,
inserting at least one dissecting instrument preferably through a second trocar,
dissecting an area of the intestine,
cutting the patient's intestine along a mutual contact line of laterally adjacent sections of a bent portion thereof and connecting by suturing and/or stapling the resulting upper and lower halves of the intestine so as to form an intestinal wall of a reservoir,
implanting at least a pump as part of a flow control device so as to permanently reside inside the patient's body and to act on said intestinal wall so as to reduce the reservoir's volume in order to empty intestinal contents from the reservoir to outside the patient's body,
extracting the instruments, camera and trocar, and in relation thereto
suturing, if necessary, the abdominal wall and permanently closing the skin.

As also mentioned before, the system may be surgically connected to a surgically created stoma or to the patient's rectum or anus or to tissue adjacent the patient's anus. This would require, where a stoma is involved, the following additional steps:

cutting the patient's skin and abdominal wall so as to create an opening for an intestinal stoma,
dissecting the area of the opening,
dividing the intestine downstream of the reservoir so as to maintain an upstream natural intestine section still connected to the reservoir with a cross-sectional opening at the downstream end thereof,
dissecting the mesentery of the upstream natural intestine section in the area of the cross-sectional opening at the downstream end thereof to prepare for creating the intestinal stoma,
advancing the upstream natural intestine section through the abdominal wall and skin and
suturing the upstream natural intestine section in the area of the cross-sectional opening to the skin with the intestinal mucosa turned inside out, thereby achieving the intestinal stoma.

Where the system may be surgically connected to a the patient's anus or to tissue adjacent the patient's anus, this would require the following additional steps:

dividing the intestine so as to create an upstream natural intestine section having a cross-sectional opening at the downstream end thereof and a downstream natural intestine section leading to the patient's anus,
dissecting the area of the patient's anus and surgically separating the downstream natural intestine section from the patient's anus, whereas the steps of dividing the intestine and separating the intestine section leading to the patient's anus can alternatively be carried out in reversed order,
dissecting the mesentery of the upstream natural intestine section in the area of the cross-sectional opening at the downstream end thereof to prepare for connecting the upstream natural intestine section to the patient's anus or tissue adjacent the patient's anus,
advancing the downstream end of the upstream natural intestine section through the patient's anus, and
suturing the cross-sectional opening of the upstream natural intestine section to the patient's anus or tissue adjacent the patient's anus.

In context with the implantation of an electrical stimulation type pump described previously, the method may further involve the step of implanting at least one holding device with electrodes in the vicinity of the intestinal reservoir so as to allow for at least partial contraction of the intestinal reservoir by means of electrical stimulation of muscle or neural tissue with the aid of the electrodes of the holding device. Preferably, electric pulses are applied to the intestine section by means of the stimulation device.

According to a preferred embodiment, as also mentioned before, folds are surgically created from the intestinal wall of the reservoir and components of the electrical stimulation type pump are implanted in the folds. The open side of the folds is preferably closed by sewing, bonding and/or stapling the tissue of the intestinal wall together so as to form bags in which the holding devices of the pump are placed either after or preferably before the closing of the folds. While the holding devices are preferably longitudinal, they may likewise have any other shape, whereby the folds or bags are surgically formed from the intestinal wall so as to accommodate therein the individual stimulation devices.

Preferably, a plurality of holding devices is implanted side by side along the intestinal wall of the reservoir so as to be able to stimulate different portions of the intestinal wall over time. More specifically, the stimulation devices may be implanted to pump intestinal contents along the intestinal reservoir by, over time, stimulating the different portions of the intestinal wall consecutively or, preferably, in a wave like manner.

Alternatively, or in addition to the electrical stimulation type pump, a constriction type pump, such as a mechanical pump or a hydraulic pump, may be implanted so as to allow for at least partial mechanical or hydraulic constriction of the intestinal reservoir by means of the constriction type pump. The constriction type pump may advantageously be combined with the electrical stimulation type pump so as to allow for adding further constriction of the intestinal reservoir by stimulating sections of the intestinal reservoir with electric pulses. In particular, this may be used for pumping intestinal contents along the intestinal reservoir by, over time, stimulating the different portions of the intestine section in a wave-like manner, when constriction of the intestine section caused by the constriction device is released.

EXIT and ENTRY VALVE

Where an exit valve is provided in addition to the at least one pump for preventing intestinal contents to exit the intestinal reservoir unintentionally, the method of implantation preferably comprises the additional step of placing the exit valve outside and adjacent to a section of the intestine downstream of the intestinal reservoir so as to allow acting on said intestine section from the outside thereof by means of the exit valve.

Similarly, where an entry valve is provided for preventing backflow of intestinal contents from the reservoir when the intestinal reservoir is being emptied, the method of implantation may further comprise the additional step of placing the entry valve outside and adjacent to a section of the intestine upstream of the intestinal reservoir so as to allow acting on said intestine section from the outside thereof by means of the entry valve.

It should be noted that any embodiment or part of embodiment or feature or method or part of method or system or part of system may be combined in any possible way and that method and apparatus features may be interchanged.

The invention claimed is:

1. A system for treating a patient having a disorder related to a patient's intestine and further having a reservoir which is provided for receiving and temporarily collecting therein intestinal contents, the reservoir being formed from surgically modified intestine that has been cut along a mutual contact line of laterally adjacent sections of a bent portions of intestine and connected so that the resulting upper and lower halves of the bent portions of intestine form an intestinal wall of the reservoir, the reservoir having an entry and an exit for the intestinal contents to enter into and exit from the reservoir and further having a length between the entry and the exit and a width of 10 cm or more, wherein the system comprises an artificial flow control device implantable in the patient's body and adapted to control flow of the intestinal contents from said reservoir, the flow control device comprising at least one pump adapted to act on said intestinal wall so as to reduce the reservoir's volume, thereby emptying the reservoir, wherein the at least one pump comprises a pump adapted to act on said intestinal wall from outside of the reservoir so as to empty the reservoir by squeezing the reservoir from the outside thereof, (a) wherein the at least one pump comprises a hydraulic pump, a hydraulically acting member for acting on said intestinal wall from the outside of the reservoir, and an artificial reservoir, wherein the hydraulic pump is adapted to pump hydraulic fluid from the artificial reservoir to the hydraulically acting member, wherein the hydraulically acting member is configured to accommodate the reservoir therein, or (b) wherein the at least one pump comprises at least one mechanically acting member for acting on said intestinal wall from the outside of the reservoir and a motor adapted to drive the at least one mechanically acting member for emptying the reservoir, wherein the at least one mechanically acting member is a roller adapted to be rolled over the reservoir for emptying the reservoir.

2. The system according to claim 1, wherein the hydraulically acting member comprises a plurality of hydraulic chambers.

3. The system according to claim 2, wherein each hydraulic chamber of said plurality of hydraulic chambers is hydraulically interconnected with respectively two other hydraulic chambers of said plurality of hydraulic chambers, except a first hydraulic chamber and a last hydraulic chamber which are hydraulically connected to the artificial reservoir and to only one other hydraulic chamber of said plurality of hydraulic chambers.

4. The system according to claim 3, wherein the plurality of hydraulic chambers are interconnected by holes acting as throttles for the hydraulic fluid.

5. The system according to claim 3, comprising one or more actively controlled valves between interconnected hydraulic chambers.

6. The system according to claim 3, wherein one or all of the plurality of hydraulic chambers are arranged such that they can be hydraulically isolated from other hydraulic chambers by individually controlling respective valves within a hydraulic path.

7. The system according to claim 2, wherein one or all of the plurality of f hydraulic chambers are arranged such that they are hydraulically isolated from other hydraulic chambers and connected to the hydraulic pump via individual hydraulic control lines.

8. The system according to claim 2, wherein only a first hydraulic chamber and a last hydraulic chamber of the plurality of hydraulic chambers are hydraulically connected to the artificial reservoir by hydraulic conduits.

9. The system according to claim 1, wherein the hydraulic pump is adapted to evacuate the hydraulically acting member by applying negative pressure.

10. The system according to claim 1, comprising at least one valve between the hydraulically acting member and the artificial reservoir, which, when in an appropriate operational position, allows the hydraulic fluid to passively flow from the hydraulically acting member back into the artificial reservoir when the reservoir fills with intestinal contents and which, when in an appropriate other position, prevents the hydraulic fluid from flowing from the hydraulically acting member back into the artificial reservoir when the reservoir is being emptied.

11. The system according to claim 1, wherein the roller is a first roller, and wherein the system further comprises a second two rollers, and wherein the first and second rollers are adapted to act simultaneously on opposite sides of the reservoir.

12. The system according to claim 1, wherein said rollers is adapted to act on one side of the reservoir against a counteracting plate adapted to be arranged on an opposite side of the reservoir.

13. The system according claim 1, comprising at least two tracks for guiding the roller when driven by the motor.

14. The system according to claim 13, wherein the at least two tracks each have a bent end portion so arranged that the bent end portion directs away from the reservoir when implanted.

* * * * *